United States Patent
Vanassche et al.

(10) Patent No.: US 11,104,569 B2
(45) Date of Patent: Aug. 31, 2021

(54) BEVERAGE DISPENSING SYSTEM FOR SPORTS DRINKS WITH PERSONALIZED HYDRATION SOLUTIONS

(71) Applicant: THE COCA-COLA COMPANY, Atlanta, GA (US)

(72) Inventors: Raymond Vanassche, Alpharetta, GA (US); Franchot Chang, Marietta, GA (US); Joshua Schwarber, Decatur, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 16/639,361

(22) PCT Filed: Aug. 16, 2018

(86) PCT No.: PCT/IB2018/056183
§ 371 (c)(1),
(2) Date: Feb. 14, 2020

(87) PCT Pub. No.: WO2019/035043
PCT Pub. Date: Feb. 21, 2019

(65) Prior Publication Data
US 2020/0247659 A1 Aug. 6, 2020

Related U.S. Application Data

(60) Provisional application No. 62/546,339, filed on Aug. 16, 2017.

(51) Int. Cl.
*B67D 1/08* (2006.01)
*B67D 1/00* (2006.01)

(52) U.S. Cl.
CPC .......... *B67D 1/0888* (2013.01); *B67D 1/0021* (2013.01); *B67D 1/0882* (2013.01);
(Continued)

(58) Field of Classification Search
CPC .. B67D 1/0888; B67D 1/0021; B67D 1/0882; B67D 2001/0827; B67D 2210/00089; A61B 5/0537
See application file for complete search history.

(56) References Cited

U.S. PATENT DOCUMENTS 10,399,838 B2 * 9/2019 Green ................... B67D 1/0864
10,800,643 B2 * 10/2020 Gatipon ................ B67D 1/004
(Continued)

FOREIGN PATENT DOCUMENTS

WO 2016-141322 A1 9/2016

OTHER PUBLICATIONS

International Search Report and Written Opinion issued by the International Searching Authority (ISA/KR) in PCT Application No. PCT/IB2018/056183 dated Dec. 6, 2018. 11 pages.
(Continued)

*Primary Examiner* — Donnell A Long
(74) *Attorney, Agent, or Firm* — Meunier Carlin & Curfman LLC

(57) ABSTRACT

The present application provides a beverage dispensing system for providing a personalized sports drink with one or more additives based on biometric data. The beverage dispensing system may include an input section for the biometric data, an analytics section for analyzing the biometric data and providing a recipe for the personalized sports drink based upon the analysis, and a beverage dispenser for dispensing the personalized sports drink. The beverage dispenser may include a number of cartridges with the one or more additives therein.

16 Claims, 5 Drawing Sheets

(52) U.S. Cl.
CPC ............... *B67D 2001/0827* (2013.01); *B67D 2210/00089* (2013.01)

(56) References Cited

U.S. PATENT DOCUMENTS

| | | |
|---|---|---|
| 2005/0133420 A1* | 6/2005 | Rinker .................... C02F 1/00 210/143 |
| 2007/0073557 A1 | 3/2007 | Abramson |
| 2007/0205221 A1 | 9/2007 | Carpenter et al. |
| 2011/0121032 A1 | 5/2011 | Deo et al. |
| 2011/0123688 A1 | 5/2011 | Deo et al. |
| 2011/0264285 A1 | 10/2011 | Mattos, Jr. et al. |
| 2016/0090288 A1 | 3/2016 | Givens et al. |
| 2016/0157749 A1 | 6/2016 | Bohorquez et al. |
| 2017/0022043 A1 | 1/2017 | Newman et al. |
| 2017/0225936 A1* | 8/2017 | Jersey ..................... F25C 5/20 |

OTHER PUBLICATIONS

Supplementary European Search Report for European Application No. 18847009 dated Apr. 8, 2021.
First Office Action received in connection with Chinese Application No. 201880059345.0 dated May 6, 2021, 13 pages.

* cited by examiner

BEVERAGE DISPENSING SYSTEM FOR SPORTS DRINKS WITH PERSONALIZED HYDRATION SOLUTIONS

This application is a national stage application filed under 35 U.S.C. § 371 of PCT/IB2018/056183, filed Aug. 16, 2018, which claims the benefit of U.S. Provisional Patent Application Ser. No. 62/546,339 filed Aug. 16, 2017, the disclosures of which are expressly incorporated herein by reference.

TECHNICAL FIELD

The present application and the resultant patent relate generally to a beverage dispensing system and more particularly relate to a beverage dispensing system using biometric and other types of data to provide a sports drink with personalized hydration solutions to athletes and other types of consumers.

BACKGROUND OF THE INVENTION

Sports drinks, such "POWERADE®" sports drinks offered by The Coca-Cola Company of Atlanta, Ga., are popular with consumers for providing proper hydration with great taste. Sports drinks may be favored by non-athletes and athletes alike and from casual athletes to professional athletes. Specifically, high school, college, and professional sports team place considerable emphasis on maintaining proper athlete hydration. Sports drinks typically may include electrolytes lost during perspiration. For example, "POWERADE ION4®" sports drinks may provide electrolytes such as sodium, potassium, magnesium, and calcium.

Trainers and the like may monitor an athlete's biometric data and nutritional intake to promote peak performance. This data may include weight, hydration level, heart rate, water intake, carbohydrate intake, protein intake, supplement intake, sodium intake, blood pressure, expended and intended exertion, temperature, blood oxygen levels, and other metrics. Trainers thus may seek to tailor a given type of sports drink with a number of additive for a specific athlete or a specific type of athlete. Mixing such additives for a number of athletes, however, may be a time consuming process, particularly during a game or on the practice field.

SUMMARY OF THE INVENTION

The present application and the resultant patent thus provide a beverage dispensing system for providing a personalized sports drink with one or more additives based on biometric data. The beverage dispensing system may include an input section for the biometric data, an analytics section for analyzing the biometric data and providing a recipe for the personalized sports drink based upon the analysis, and a beverage dispenser for dispensing the personalized sports drink. The beverage dispenser may include a number of cartridges with the one or more additives therein.

The present application and the resultant patent further provide a beverage dispenser for providing a personalized sports drink with one or more additives. The beverage dispenser may include a number of cartridges with the one or more additives therein and a dispenser graphical user interface. The dispenser graphical user interface may include a number of personalization scales to allow a user to vary a level of carbohydrates, a level of intensity, a level of sweetness, and/or the one or more additives therein.

These and other features and improvements of the present application and the resultant patent will become apparent to one of ordinary skill in the art upon review of the following detailed description when taken in conjunction with the several drawings and the appended claims.

DETAILED DESCRIPTION

Figure 1:
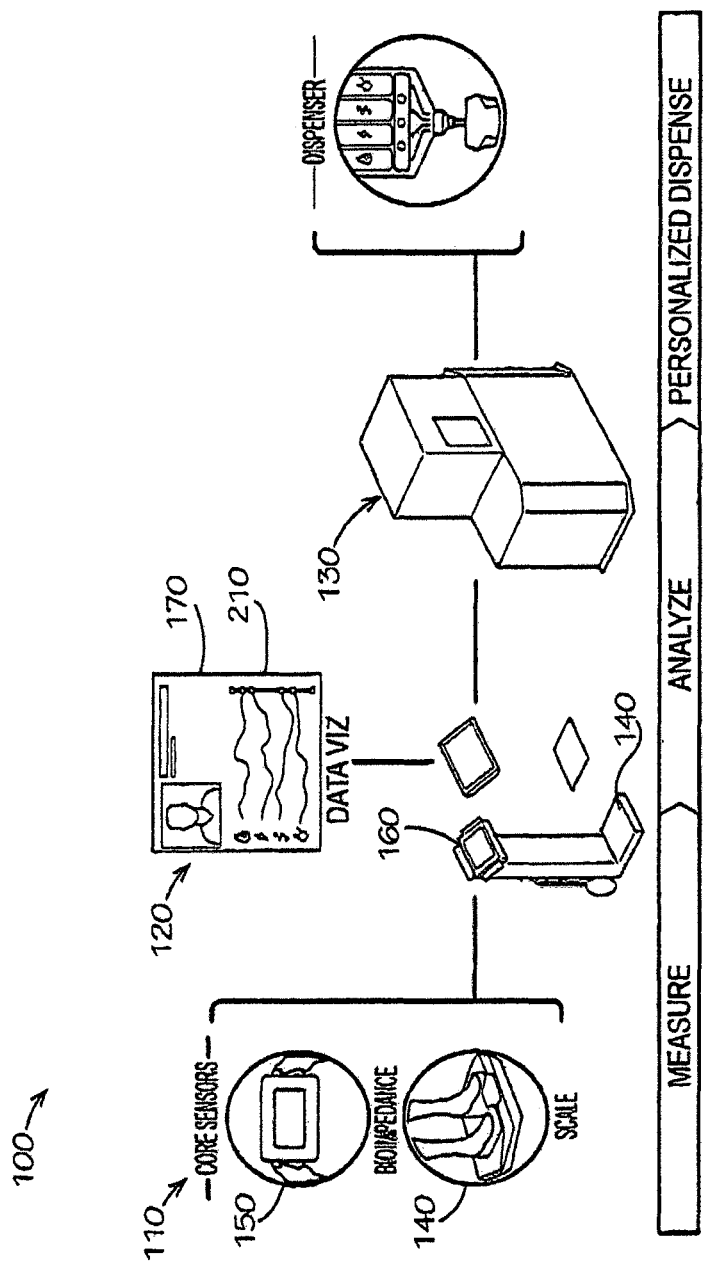
FIG. 1 is a perspective view of an example of a beverage dispensing system as may be described herein.
Figure 2:
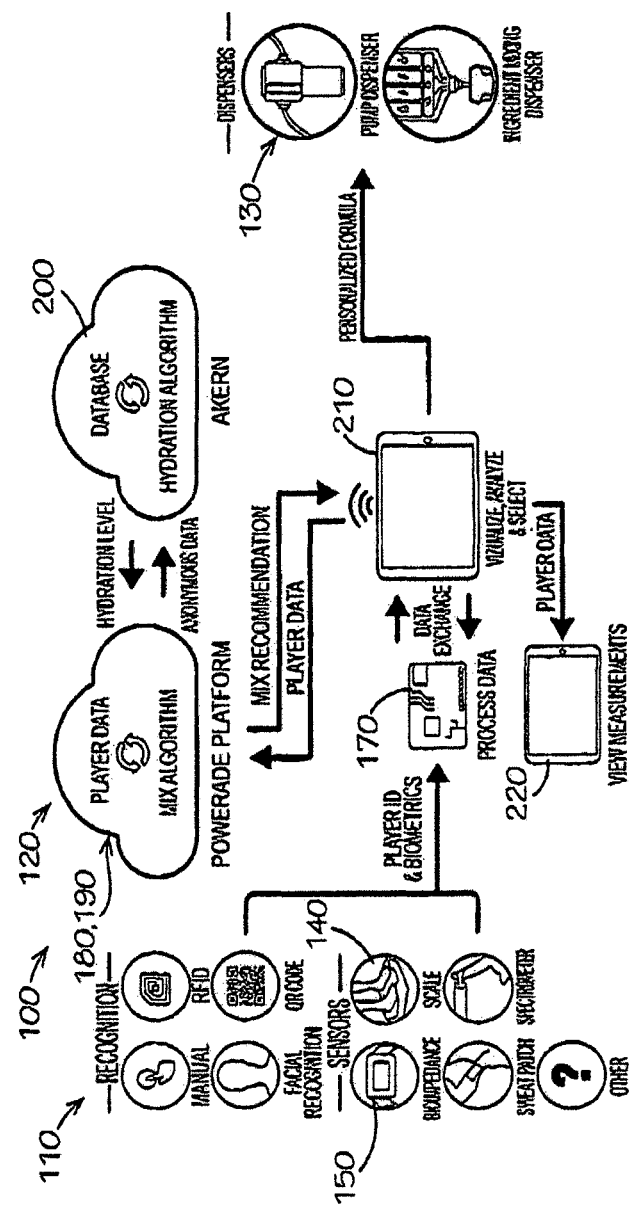
FIG. 2 is a schematic diagram of the functionality of the beverage dispensing system of FIG. 1.

Referring now to the drawings, in which like numerals refer to like elements throughout the several views, FIG. 1 and FIG. 2 show an example of a beverage dispensing system 100 as may be described herein. The beverage dispensing system 100 may dispense personalized sports drinks as well as many different types of beverages, other types of fluids, and/or other types of products. Generally described, the beverage dispensing system 100 may include three main sections: an input section 110, an analytics section 120, and a beverage dispenser 130. Other sections and other types of functionality may be used herein.

The input section 110 may receive many types of biometric and other types of data. As described above, this biometric data may include weight, hydration level, heart rate, water intake, carbohydrate intake, protein intake, supplement intake, sodium intake, blood pressure, expended and intended exertion, temperature, blood oxygen levels, and other metrics. This data may be gathered from a weight scale 140, different types of sensors 150, or direct input on an input graphical user interface 160 such as a touch screen and the like. The sensors 150 may include, for example, bioimpedance sensors, spectrometers, sweat or other types of smart patches, wearable devices such as accelerometers, step counters, GPS, and any device the detects the activity and/or physical condition of the user. Other sensor 140 may be used for localized conditions such as time, temperature, weather, location, type of workout, and the like. Input from any number of sensors 150 or other types of input sources may be used together. The sensors 150 also may be built into the workout equipment, uniforms, beverage bottles, and the like. Any type of data from any source may be used herein. Users may be identified individually by name, by player number, or by any type of identifier. Identification may be made by user input, code, RFID, Bluetooth, smartphone, or any conventional manner. The input graphical user interface 160 may allow a user to input data and/or select any number of different beverage or product brands, types, and/or formulations as well as provide individual preferences. Other components and other configurations may be used herein.

The analytics section 120 may include a controller or a processor 170 coupled to one or more databases 180 or other types of memory. The processor 170 may be any type of programmable logic device. The processor 170 may be local or remote. Multiple processors 170 may be used herein. The processor 170 may execute computer-executable program instructions stored in the databases 180. The computer executable program instructions may include any number of module application programs required to operate the beverage dispensing system 100. Specifically, the databases 180 may include code instructions, information structures, and the like. Such instructions and information structures may embody or constitute machine-learning techniques (e.g., pattern recognition algorithms; inference algorithms; triangulation or location estimation algorithms; temporal algorithms; and the like) that may be utilized to implement the functionality described herein.

In this example, the analytics section 120 may include a player data database 190 and a consumption database 200. Player data from the input section 110 may be stripped of individual identification and compared in the consumption database 200 via a hydration algorithm to determine particular hydration needs. Smart learning techniques may be used over time to improve overall accuracy. The particular hydration needs determined in the consumption database 200 may be returned to the player database 190 and compared therein via a mix algorithm to determine an appropriate sports drink mix or recipe. Specifically, the type of beverage as well as the level of carbohydrates, sweetener, electrolytes, proteins, supplements, and the like may be determined. Certain ingredients may be time released for extended performance. The temperature of the beverage also may be determined. Other types of algorithms and other types of output may be used herein. An output graphical user interface 210 may be used to display the recipe, the ingredients, the amount of ingredients, calories, and the like. A log 220 also may be used with a history of player data, beverage date, performance data, and the like. Other components and other configurations may be used herein.

Figure 3:
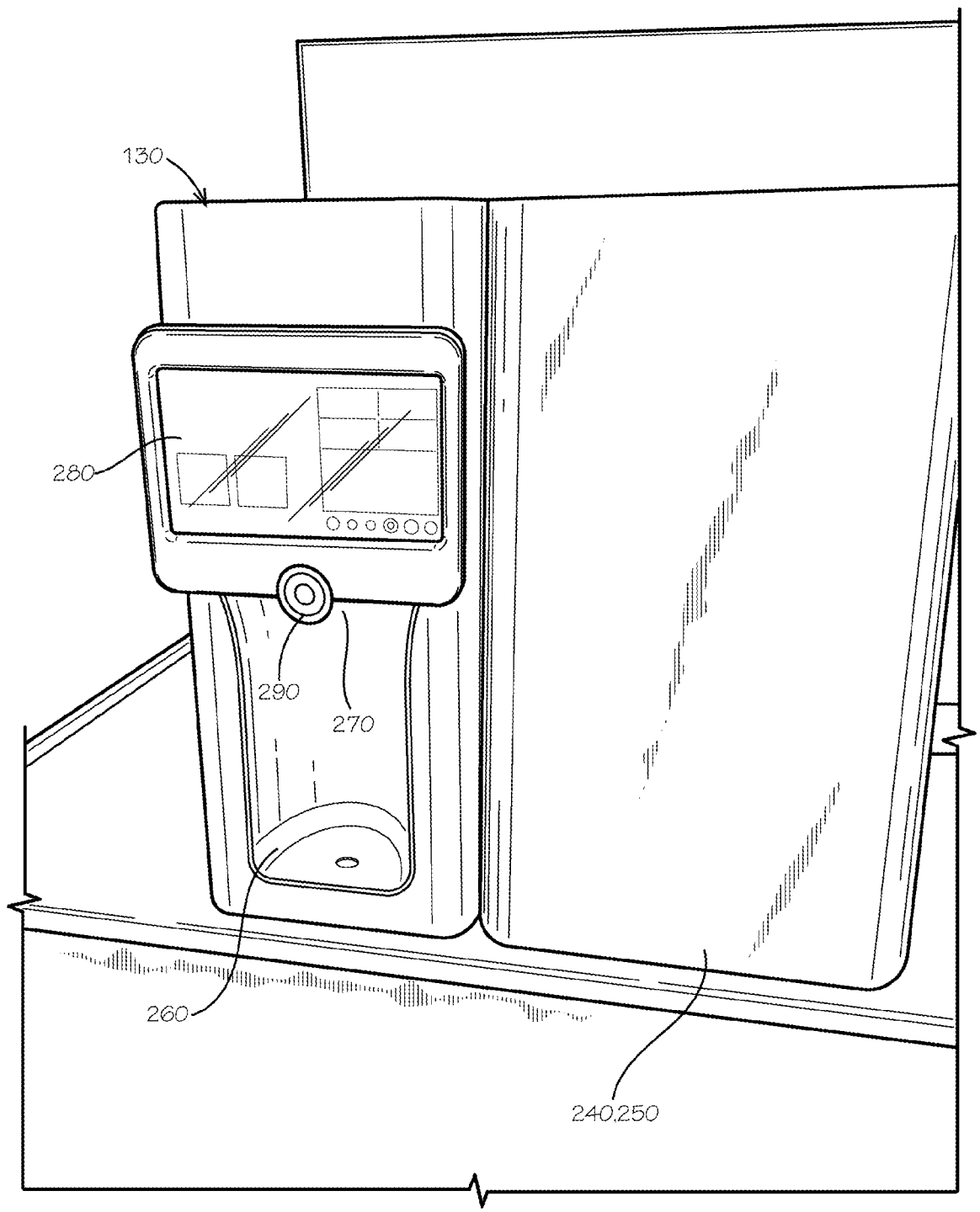
FIG. 3 is a perspective view of a beverage dispenser that may be used with the beverage dispensing system of FIG. 1.
Figure 4:
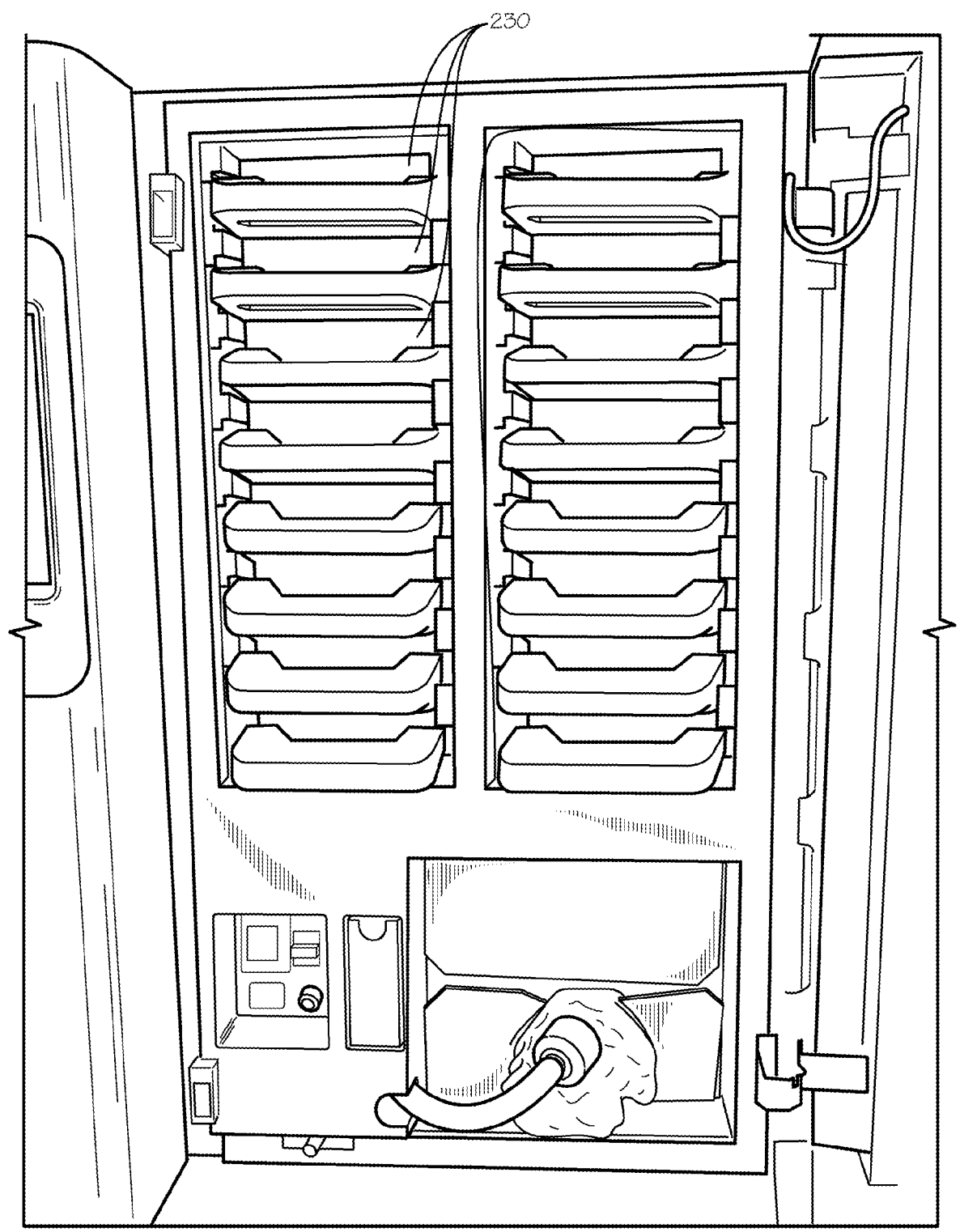
FIG. 4 is a perspective view of the internal components of the beverage dispenser of FIG. 3.
Figure 5:
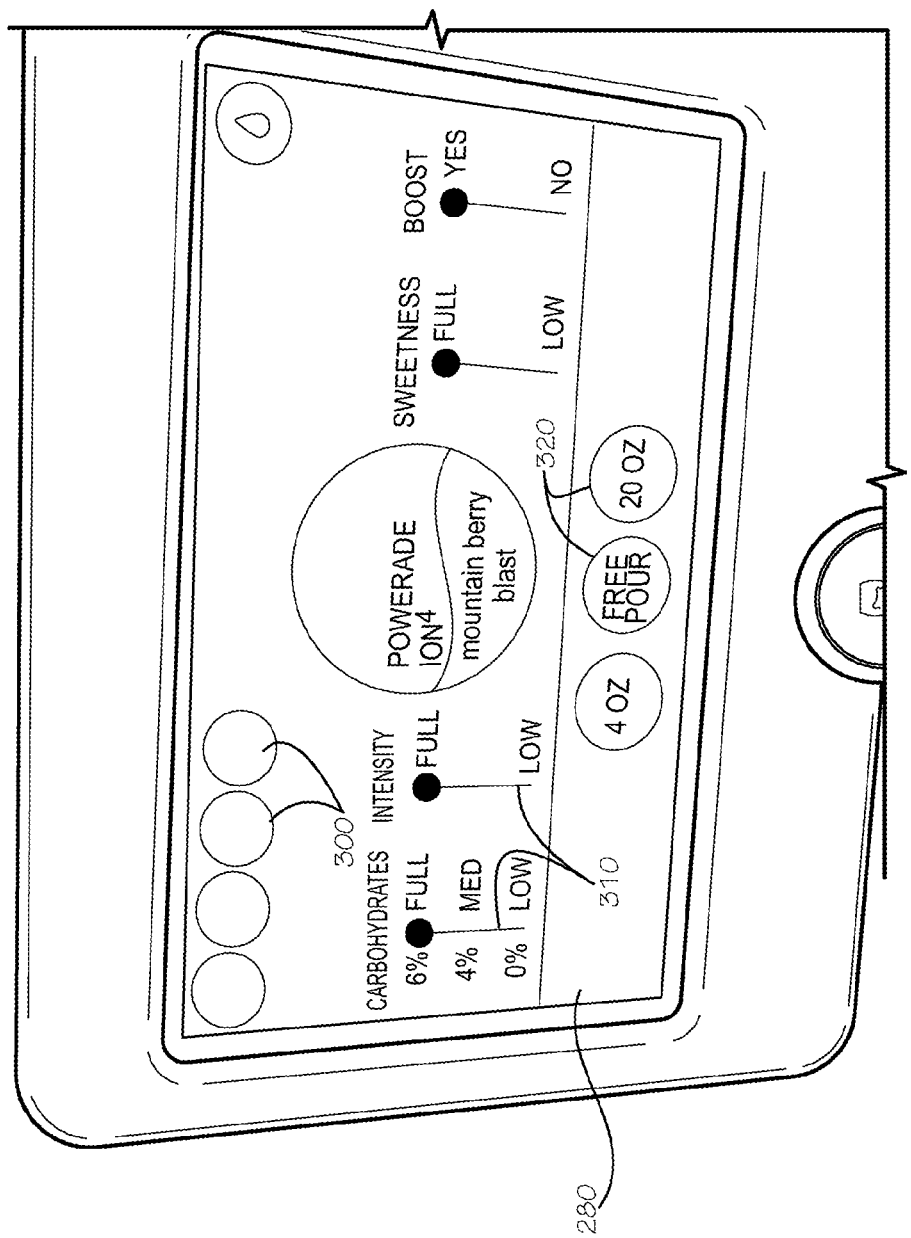
FIG. 5 is a perspective view of a graphical user interface for use on the beverage dispenser of FIG. 3.

FIGS. 3-5 show an example of the beverage dispenser 130 that may be used in the beverage dispensing system 100 described herein. The beverage dispenser 130 may be the "COCA-COLA FREESTYLE®" refrigerated beverage dispensing unit offered by The Coca-Cola Company of Atlanta, Ga. Generally described, the "COCA-COLA FREESTYLE®" refrigerated beverage dispensing unit creates a beverage by combining a number of highly concentrated micro-ingredients with a macro-ingredient such as a sweetener and a diluent. The micro-ingredients and other additives generally are stored in cartridges 230 positioned within the beverage dispenser itself. The number and type of beverages offered by the beverage dispenser 100 thus may be limited only by the number and type of cartridges 230 positioned therein. Alternatively, convention bag-in-box based beverage dispensers and the like also may be used herein.

The beverage dispenser 130 may include an outer shell 240 with an access door 250. The cartridges 230 and other types of beverage ingredients may be loaded through the access door 250. In addition to the micro-ingredients, the cartridges 230 also may contain different types of additives, sweeteners, flavoring, coloring, and the like. As is shown in FIG. 4, the cartridges 230 may contain electrolytes such as sodium, potassium, magnesium, and calcium. Proteins, supplements, and the like also may be used. The additives generally may be in the form of micro-ingredients. The outer shell 240 may define a dispensing area 260 with one or more dispensing nozzles 270. The beverage dispenser 130, and the components thereof, may have any suitable size, shape, or configuration.

The beverage dispenser 130 may include a dispenser graphical user interface 280 positioned thereon. The dispenser graphical user interface 280 may include a touch screen and the like so as to allow a consumer to select any number of different beverage or product brands, types, and/or formulations. The dispenser graphical user interface 280 may present the consumer with a series of dynamically generated menus and/or static menus. Selecting a menu item may cause the beverage dispenser 130 to formulate and dispense the beverage. The dispenser graphical user interface 280 also may display any type of graphics, messaging, video, and the like. Sound also may be incorporated herein. One or more separate display screens, banner screens, and the like also may be used. Different types of mechanical and/or electro-mechanical push buttons, such as a pour button 290, also may be used. Other components and other configurations also may be used herein.

The beverage dispenser 130 may be in communication with the input section 110 and the analysis section 120. Specifically, the personalized beverage type and ingredients determined in the analytics section 120 based upon the data from the input section 110 may be sent to the beverage dispenser 130 to be dispensed therefrom. Alternatively, the beverage type and ingredients may be stored remotely or locally for access by the beverage dispenser 130. Further, the user may provide the beverage type and ingredients to the beverage dispenser 130 via, for example, smart phone, Bluetooth, RFID, and the like. Any conventional communication method may be used to deliver the selected beverage type and ingredients to the beverage dispenser 130. Other components and other configurations may be used herein.

Alternatively, the user may select the type of beverage and other beverage characteristics directly on the dispenser graphical user interface 280. FIG. 5 shows one example of the dispenser graphical user interface 280. The dispenser graphical user interface 280 may include a number of brand selection icons 300. In the example, the brand selection icons 300 include different flavors of "POWERADE ION4®" sports drinks. As is shown a "MOUNTAIN BERRY BLAST" flavor has been chosen. The dispenser graphical user interface 280 also has a number of personalization scales 310. In this example, the user may select between full and low carbohydrates, between full and low intensity, between full and low sweetness, and whether to add boost ingredient (as above, examples include electrolytes such as sodium, potassium, magnesium, and calcium) or not. Other types of ingredients and intensities also may be used herein. A number of pour icons 320 as may be used. The user thus may customize his or her sports drink as desired. Other components and other configurations may be used herein.

The beverage dispensing system 100 thus provides the user with a personalized sports drink. The nature of the sports drink may be based on the user's biometric data and/or individual preferences. The beverage dispensing system 100 may use the biometric data for real time analysis of the user's hydration needs and produce a sports drink tailored to those real time needs. Such real time analysis and production may provide the user with improved and/or maintained athletic performance. Likewise, maintaining proper hydration may avoid injuries and downtime.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

We claim:

1. A beverage dispensing system for providing a personalized sports drink with one or more additives based on biometric data, comprising:
   an input section for the biometric data;
   an analytics section for analyzing the biometric data and providing a recipe for the personalized sports drink based upon the analysis, wherein the recipe comprises one or more micro-ingredient flavors, a sweetener, a diluent, and the one or more additives, and wherein the analytics section determines a type of beverage as well as a level of the one or more additives; and
   a beverage dispenser for dispensing the personalized sports drink;
   wherein the beverage dispenser comprises a plurality of cartridges with the one or more micro-ingredient flavors and the one or more additives therein.

2. The beverage dispensing system of claim 1, wherein the input section comprises a plurality of sensors.

3. The beverage dispensing system of claim 2, wherein the plurality of sensors comprises a scale.

4. The beverage dispensing system of claim 2, wherein the plurality of sensors comprises a bioimpedance sensor.

5. The beverage dispensing system of claim 2, wherein the plurality of sensors comprises a wearable sensor.

6. The beverage dispensing system of claim 1, wherein the input section comprising an input graphical user interface.

7. The beverage dispensing system of claim 1, wherein the analytics section comprises a processor and one or more databases.

8. The beverage dispensing system of claim 7, wherein the one or more databases comprises one or more algorithms to determine the recipe of the personalized sports drink.

9. The beverage dispensing system of claim 1, wherein the one or more additives in the plurality of cartridges comprise electrolytes.

10. The beverage dispensing system of claim 1, wherein the one or more additives in the plurality of cartridges comprise proteins.

11. The beverage dispensing system of claim 1, wherein the beverage dispenser comprises a dispenser graphical user interface.

12. The beverage dispensing system of claim 11, wherein the dispenser graphical user interface comprises a plurality of brand selection icons.

13. The beverage dispensing system of claim 11, wherein the dispenser graphical user interface comprises a plurality of personalization scales.

14. The beverage dispensing system of claim 13, wherein the plurality of personalization scales allow a user to vary a level of carbohydrates, a level of intensity, a level of sweetness, and/or the one or more additives.

15. A beverage dispenser for providing a personalized sports drink with one or more additives, comprising:
   an input section for biometric data;
   an analytics section for analyzing the biometric data and providing a recipe for the personalized sports drink based upon the analysis, wherein the recipe comprises the one or more additives;
   a plurality of cartridges with the one or more additives therein; and
   a dispenser graphical user interface;
   wherein the dispenser graphical user interface comprises a personalization scale to allow a user to select whether or not to add the one or more additives.

16. The beverage dispenser of claim 15, wherein the graphical user interface further comprises one or more additional personalization scales to allow a user to vary a level of carbohydrates, a level of intensity, and/or a level of sweetness.

* * * * *